United States Patent [19]
Lee

[11] Patent Number: 5,133,734
[45] Date of Patent: Jul. 28, 1992

[54] PNEUMATICALLY OPERATED FEMORAL ARTERY COMPRESSOR

[75] Inventor: Ling H. Lee, Memphis, Tenn.

[73] Assignee: Wagi L.P., Memphis, Tenn.

[21] Appl. No.: 740,123

[22] Filed: Aug. 5, 1991

[51] Int. Cl.⁵ .............................. A61B 17/12
[52] U.S. Cl. ........................................ 606/201
[58] Field of Search ................. 606/201–204; 604/141, 143

[56] References Cited

U.S. PATENT DOCUMENTS

| | | | |
|---|---|---|---|
| 3,625,219 | 12/1971 | Abrams et al. | 606/203 |
| 3,779,246 | 12/1973 | Semler | 128/325 |
| 4,233,980 | 11/1980 | McRae et al. | 606/201 |
| 4,572,182 | 2/1986 | Royse | 606/201 |

Primary Examiner—C. Fred Rosenbaum
Assistant Examiner—William W. Lewis

[57] ABSTRACT

This invention discloses a pneumatically operated femoral artery compressor applying calibrated and calibrateable external pressure on the puncture site of a fermoral artery with the plunger end of a mounted pressurized syringe assembly.

5 Claims, 1 Drawing Sheet

PNEUMATICALLY OPERATED FEMORAL ARTERY COMPRESSOR

FIELD OF THE INVENTION

This invention relates generally to an apparatus to apply external calibrated and calibrateable pressure on a femoral artery after a transfemoral angiographic procedure.

BACKGROUND AND DISCLOSURE OF THE INVENTION

After each transfemoral angiographic procedure, it is always necessary to apply external pressure over the puncture site for a period ranging from fifteen to thirty minutes in order to stop the bleeding. Manual method has been the only means. In the market is a "Compressar" mechanical model which is basically a C-clamp device applying external but uncalibrated and uncalibrateable pressure over the puncture site. Ordinarily, pressure bandage or dressing devices are used after the bleeding has completely ceased. This invention discloses a more convenient, inexpensive, effort-saving, and labor-saving apparatus to stop the initial bleeding and any subsequent bleeding with external calibrated and calibrateable pressure from the plunger end of a pneumatically charged syringe assembly, as will be described more fully in the following specifications and further defined in the claims.

DESCRIPTION OF THE EMBODIMENT, ITS PARTS, AND THEIR FUNCTIONS

Figure 1:
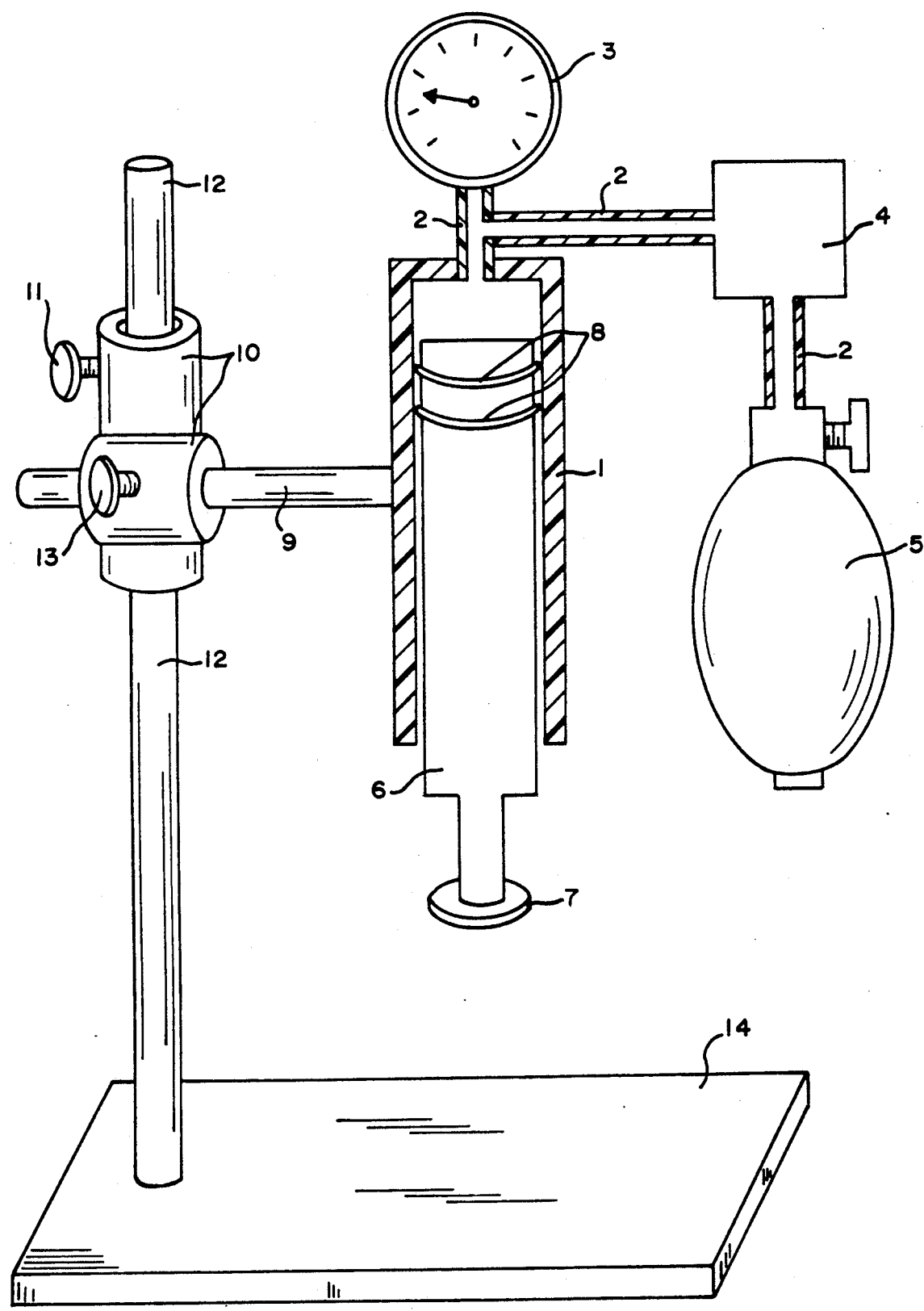
FIG. 1 is a fixed perspective and sectional view of the preferred embodiment.

Referring to FIG. 1, the vertically oriented syringe assembly has a round barrel 1 the open end of which points downward, and the upper end of which is permanently connected to the first end of a flexible tubing 2. The remaining section of tubing 2 is connected to an in-line pressure gauge 3 and also to an in-line small (approximately one hundred to two hundred millimeters) rigid air reservoir 4. The second end of the tubing 2 is permanently connected to a hand-operated bulb insufflator 5, which supplies air to barrel 1 through tubing 2. The lower end of the syringe plunger 6 of the syringe assembly is fitted with a sterile and replaceable pressure disk 7. O-rings 8 between the circumference of plunger 6 and the interior wall of barrel 1 serve as seals and yet allow piston actions between plunger 6 and barrel 1. The function of reservoir is to maintain a reasonably constant intra-barrel pressure in the event of small movements of plunger 6. As depicted, the first end of the barrel-supporting horizontally oriented rod 9 is permanently and fixedly mounted near the mid-section of barrel 1. As depicted, 10 represents a right-angle scaffold joint having a first horizontal tunnel and a second vertical tunnel The said first horizontal tunnel receives slideably the second end of supporting rod 9. 13 depicts a first hand-operated set screw on the right-angle scaffold joint 10 to fix the position of supporting rod 9 within right-angle scaffold joint 10. 12 depicts a vertically oriented pole which fits slideably in said second vertical tunnel of said right-angle scaffold joint 10. In the body of right-angle scaffold joint 10 is a second hand-operated set screw 11 which fixes the position of pole 12 within said right-angle scaffold joint 10. The lower end of pole 12 is permanently and fixedly mounted near an edge of a horizontally oriented baseboard 14.

The operation of the apparatus is as follows:

(1) deflating the air pressure in barrel 1 by opening the valve in the bulb insufflator 5;
(2) collapsing plunger 6 completely into barrel 1;
(3) by loosening set screw 11, raising the syringe assembly sufficiently to clear the hip of a supine-lying patient;
(4) placing baseboard 14 under the hip of the supine-lying patient;
(5) adjusting the position of rod 9 and right-angle scaffold joint 10 to place compressor disk 7 over the femoral artery puncture site, as knowledgeable to those skilled in the art of angiography;
(6) tightening both set screws 13 and 11;
(7) by operating bulb insufflator 5, the operator pressurizes the interior of barrel 1, as knowledgeable to those skilled in the art of angiography;
(8) extracting the catheter from the femoral artery slowly. If bleeding occurs, the operator can increase the pneumatic pressure. In an emergency situation, he loosens set screw 11, raises the syringe assembly, and removes the entire apparatus from the patient;
(9) additional visual monitoring is desirable. After the first few minutes, the operator may decrease the pneumatic pressure somewhat, in order to reduce discomfort the patient may experience. The pneumatic pressure can be adjusted up or down any time; and
(10) after the initial bleeding has stopped, the apparatus may be maintained on the patient without pressure in the syringe or with appropriate pneumatic pressure in the syringe for as long as necessary, as the physician sees fit.

Although the present invention has been described and illustrated with respect to a preferred embodiment and a preferred use, therefore, it is not to be limited since modification and changes can be made therein, which are within the full intent, scope, and spirit of the invention.

I claim:

1. For the purpose of applying external pressure on a femoral artery while and after a catheter is extracted from said femoral artery, an apparatus comprising:
   a) a vertically oriented syringe assembly having a barrel pointing upward and a plunger, having a lower end pointing downward and adapted to be in contact with the skin over the puncture site of said femoral artery and sealing means on the plunger to prevent air from escaping said barrel;
   b) a rigid air reservoir, one end of which being connected via a first flexible tubing to an upper end of said barrel and the other end of said reservoir via a second flexible tubing to a hand-operated bulb insufflator supplying air to said barrel;
   c) to monitor the pressure within said barrel, an in-line air pressure gauge connected to said first flexible tubing;
   d) a horizontally oriented rod having two ends, the first end being mounted permanently and fixedly to said barrel;
   e) a right-angle scaffold joint having two through-and-through tunnels, the first and horizontal tunnel of said scaffold joint slideable accepting the second end of said horizontally oriented rod;

f) a hand-operated set screw in the body of said right-angle scaffold joint to fix the position of said horizontally oriented rod within said first and horizontal tunnel of said right-angle scaffold joint;

g) a vertically oriented pole slideable fitting inside the second and vertical tunnel said right-angle scaffold joint;

h) a hand-operated set screw in the body of said right-angle scaffold joint to fix the position of said vertically oriented pole within said right-angle scaffold joint; and i) a horizontally oriented baseboard adapted to be placed under the hip of a supine-lying patient, said base-board near an edge being mounted permanently and fixedly to the lower end of said vertically oriented pole.

2. A method of stopping bleeding from a femoral artery while and after a catheter is extracted from said femoral artery by applying external pressure over the puncture site with the end of said plunger of said apparatus as set forth in claim 1.

3. The lower end of said plunger as set forth in claim 1 is further defined to be fitted with a sterile disk.

4. The lower end of said plunger as set forth in claim 1 is further defined to be fitted with a replaceable disk.

5. The lower end of said plunger as set forth in claim 1 is further defined to be fitted with a sterile and replaceable disk.

* * * * *